(12) United States Patent
Pekonen

(10) Patent No.: US 8,781,562 B2
(45) Date of Patent: *Jul. 15, 2014

(54) INTERFERENCE MITIGATION CIRCUITRY FOR BIOMETRIC MEASUREMENTS

(75) Inventor: Elias Pekonen, Oulu (FI)

(73) Assignee: Polar Electro Oy, Kempele (FI)

( * ) Notice: Subject to any disclaimer, the term of this patent is extended or adjusted under 35 U.S.C. 154(b) by 213 days.

This patent is subject to a terminal disclaimer.

(21) Appl. No.: 13/295,657

(22) Filed: Nov. 14, 2011

(65) Prior Publication Data

US 2012/0157867 A1   Jun. 21, 2012

(30) Foreign Application Priority Data

Dec. 17, 2010   (FI) .................................. 20106337

(51) Int. Cl.
    A61B 5/0402  (2006.01)
    A61B 5/04    (2006.01)
    A61B 5/00    (2006.01)
    A61B 5/024   (2006.01)
    A61B 5/0245  (2006.01)
    A61B 5/0428  (2006.01)
    A61B 5/0488  (2006.01)

(52) U.S. Cl.
    CPC ........... *A61B 5/0006* (2013.01); *A61B 5/02438* (2013.01); *A61B 5/0245* (2013.01); *A61B 5/04282* (2013.01); *A61B 5/0488* (2013.01); *A61B 2562/182* (2013.01)
    USPC .......................................... 600/509; 600/300

(58) Field of Classification Search
    USPC .......................................................... 607/48
    See application file for complete search history.

(56) References Cited

U.S. PATENT DOCUMENTS

2003/0006782 A1   1/2003  Shambroom et al.
2007/0270918 A1*  11/2007 De Bel et al. ................... 607/48

FOREIGN PATENT DOCUMENTS

WO    WO0065994 A1   11/2000

OTHER PUBLICATIONS

In-Duk Hwang, "Direct Interference Canceling for Two-Electrode Biopotential Amplifier", IEEE Transactions on Biomedical Engineering, vol. 55, No. 11, pp. 2620-2627, Nov. 1, 2008.
Nikola et al., "A Novel AC-Amplifier for Electrophysiology: Active DC Suppression with Differential to Differential Amplifier in the Feedback-Loop", Proceedings of the 23rd Annual EMBS International Conference, vol. 4, pp. 3328-3331, Oct. 25, 2001.
Tuomo Reiniaho, Finnish Search Report for the corresponding Finnish Application No. 20106337, pp. 1-2 (Sep. 29, 2011).

* cited by examiner

*Primary Examiner* — Carl H Layno
*Assistant Examiner* — Jon Eric C Morales
(74) *Attorney, Agent, or Firm* — Hoffmann & Baron, LLP

(57) ABSTRACT

An apparatus includes a first signal line configured to couple signals from a first skin electrode to a first input of a differential amplifier comprised as a front-stage in a signal detection circuitry for measurement of biometric signals sensed by the first skin electrode; a second signal line configured to couple signals from a second skin electrode, different from the first skin electrode, to a second input of the differential amplifier of the signal detection circuitry for measurement of biometric signals sensed by the second skin electrode; and an impedance circuitry coupled between the first signal line and the second signal line in order to tune input impedance of the differential amplifier. Impedance of the impedance circuitry is higher on a first frequency band covering a frequency band of the measured biometric signals than on a second frequency band not covering the frequency band of the measured biometric signals.

14 Claims, 7 Drawing Sheets

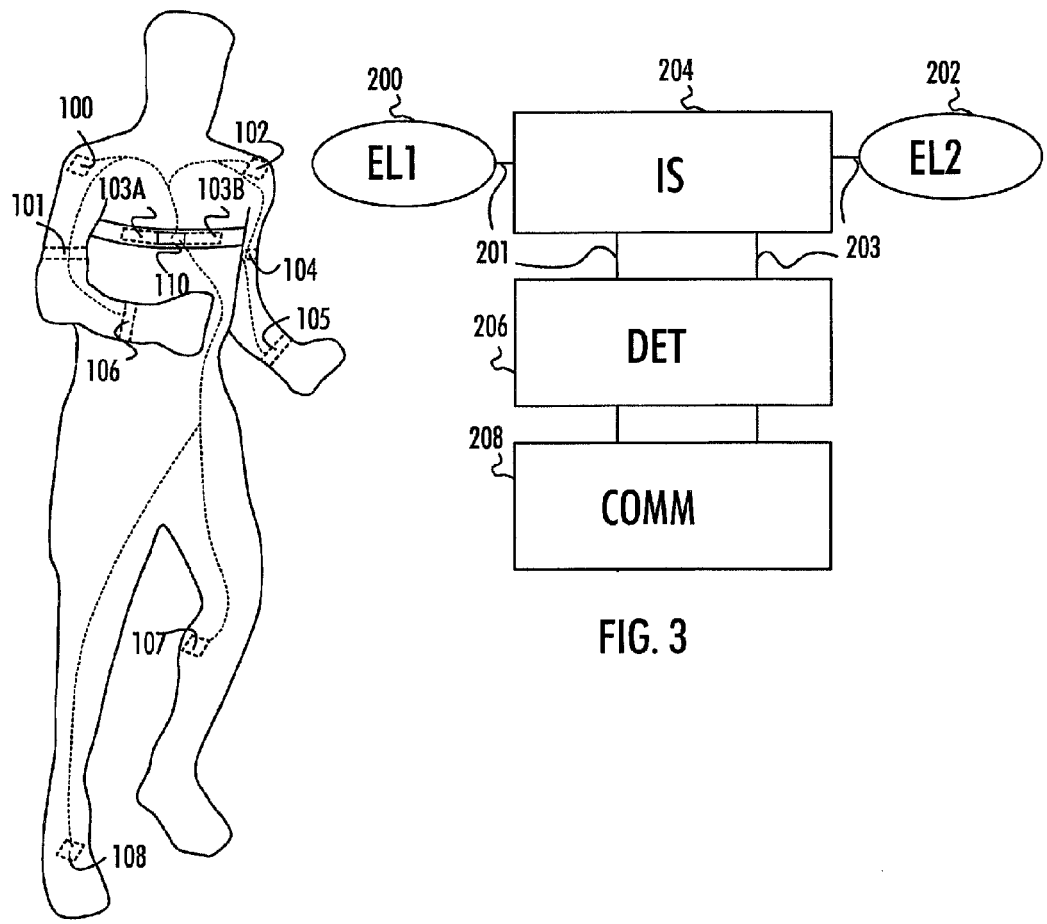
FIG. 1
FIG. 3
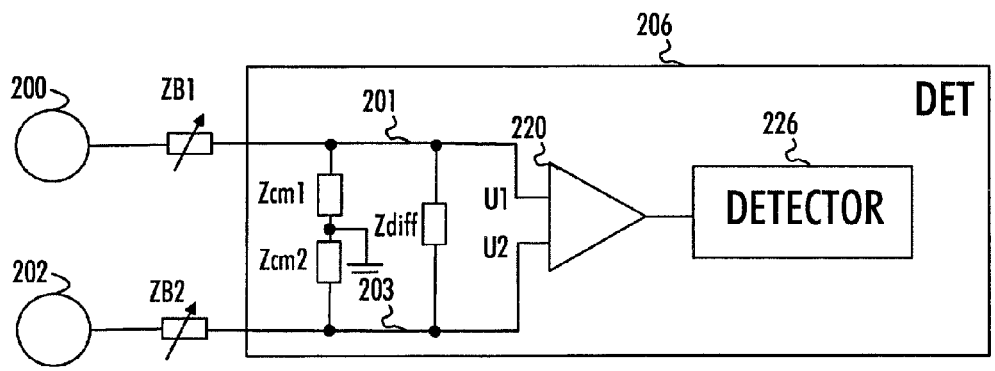
FIG. 2

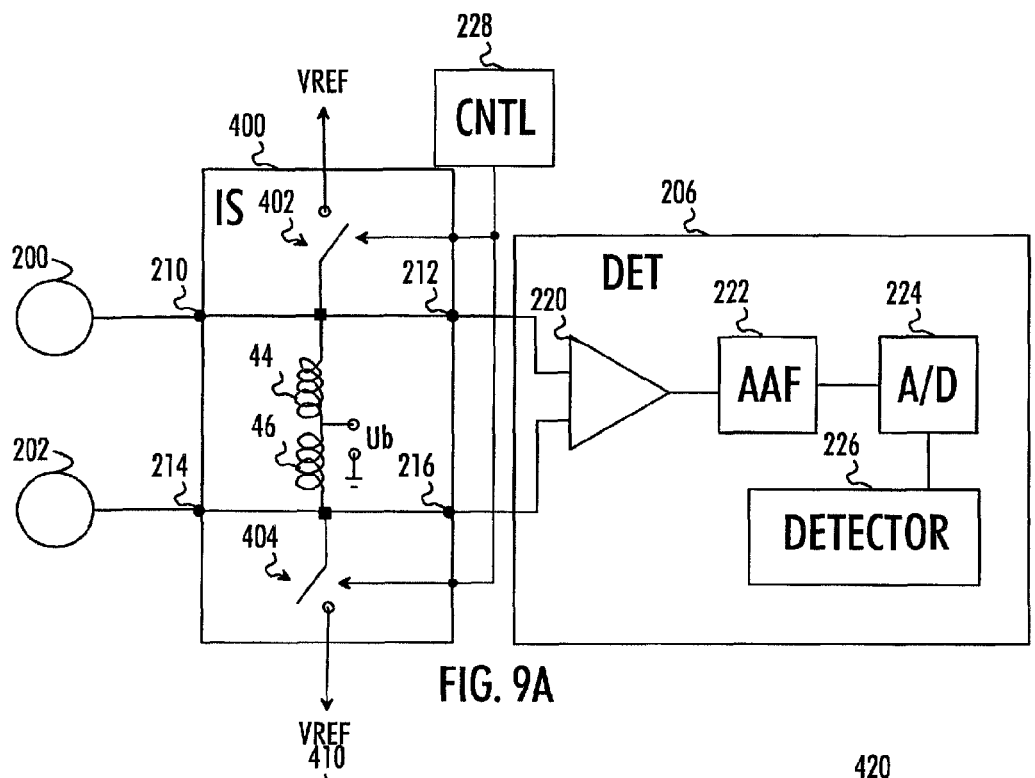
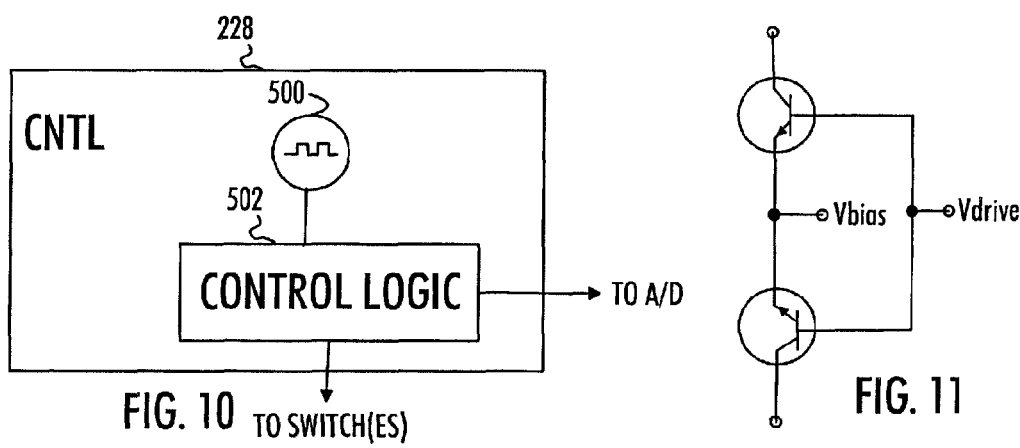

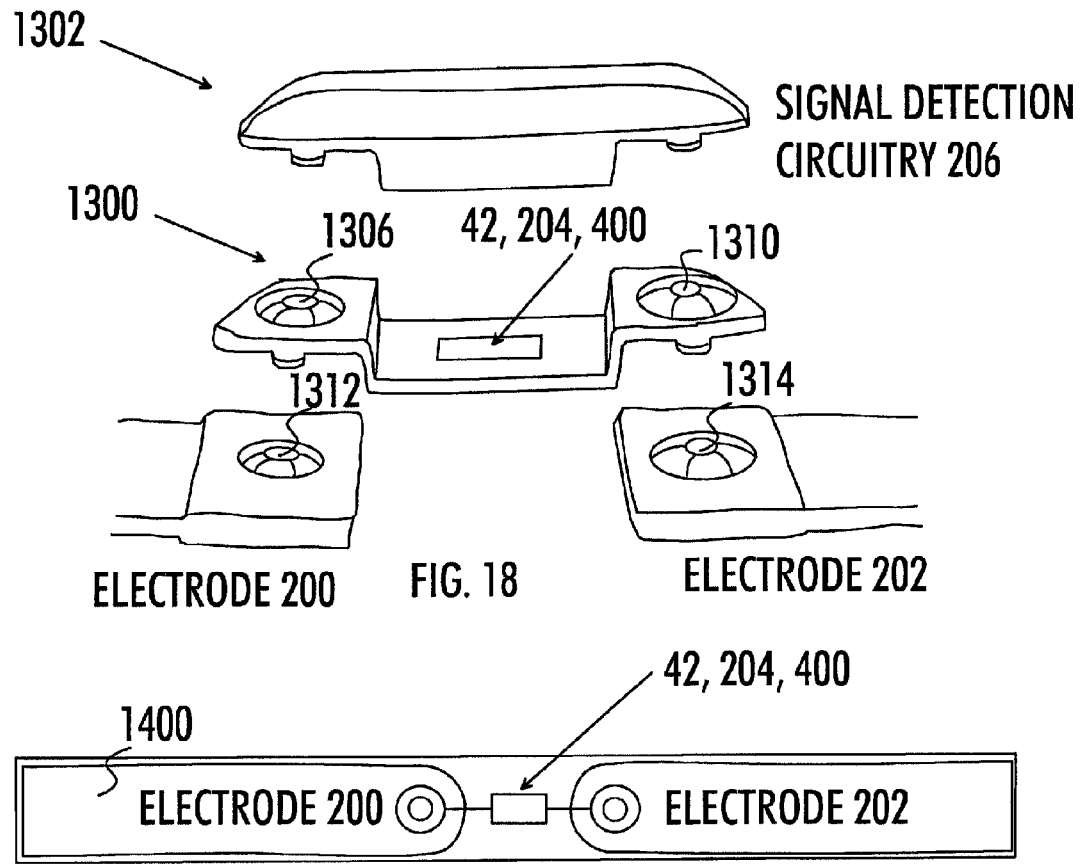
FIG. 18
FIG. 19
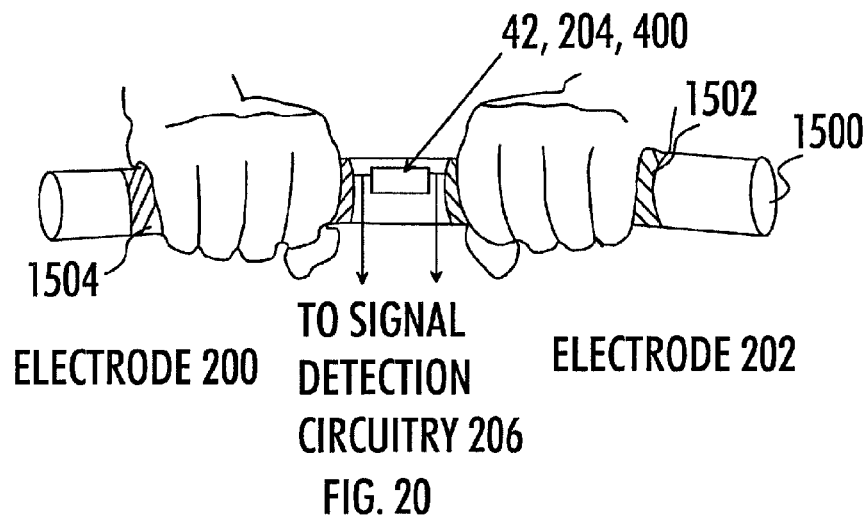
FIG. 20

INTERFERENCE MITIGATION CIRCUITRY FOR BIOMETRIC MEASUREMENTS

CROSS-REFERENCE TO RELATED APPLICATION

This application claims priority based on Finnish Application No. 20106337, filed Dec. 17, 2010, which is incorporated herein by reference.

BACKGROUND

1. Field

The invention relates to the field of measuring biometric signals.

2. Description of the Related Art

When measuring biometric signals, skin electrodes are typically in contact with the skin of a subject whose biometric signals are being measured. The skin electrodes sense electric signals, such as electrocardiographic or electromyographic signals, from the human body, and it may be understood that the contact between the skin and a skin electrode forms an impedance circuit. Particularly, when carrying out measurements on a moving body, a skin electrode may be in continuous motion with respect to the skin, and the motion causes variance in properties of the impedance circuit. It may be understood that the motion modulates the impedance of the impedance circuit, thereby causing motion artefacts superposed to the biometric signal. Typically, skin electrodes located in different parts of the body move differently with respect to the body and, accordingly, the motion artefacts may differ between two (or more) skin electrodes. This interferes with the measurement of the biometric signals.

Furthermore, human skin contains electric charges that are typically distributed non-uniformly. Additionally, the contact between the skin electrodes and the subject's skin causes a triboelectric effect, also known as triboelectric charging. The triboelectric effect is a type of contact electrification in which materials in contact with each other become electrically charged as a result of their movement with respect to each other (such as through rubbing). The polarity and strength of the charges produced differ according to the materials, surface roughness, temperature, strain, and other properties. Therefore, the triboelectric effect is different for different skin electrodes in contact with the subject. As a result of these phenomena, for example, electrical charges around one skin electrode are typically different from electrical charges around another skin electrode, which causes interference to the measurement of biometric signals.

SUMMARY

According to an aspect of the present invention, there is provided an apparatus comprising: a first signal line configured to couple biometric signals from a first skin electrode to a first input of a differential amplifier comprised as a front-stage in a signal detection circuitry for measurement of the biometric signals; a second signal line configured to couple reference signals of the biometric signals to a second input of the differential amplifier of the signal detection circuitry; and an impedance circuitry coupled between the first signal line and the second signal line, wherein impedance of the impedance circuitry is higher on a first frequency band covering a frequency band of the measured biometric signals than on a second frequency band outside the frequency band of the measured biometric signals.

According to another aspect of the present invention, there is provided a heart rate measurement unit comprising: at least one skin electrode; a signal detection circuitry comprising a differential amplifier having its inputs operationally connected to the at least one skin electrode and to a reference voltage source, and a signal detector operationally connected to an output of the differential amplifier and configured to detect a waveform from a signal received from the output of the differential amplifier, wherein the heart rate measurement unit further comprises an impedance circuitry connected to an input of the signal detection circuitry and coupled between the at least one skin electrode and the reference voltage source, wherein impedance of the impedance circuitry is higher on a first frequency band covering a frequency band of measured biometric signals than on a second frequency band outside the frequency band of the measured biometric signals.

According to another aspect of the present invention, there is provided an apparatus comprising: a casing; a plurality of connectors connecting the apparatus between a plurality of skin electrodes and a casing of a signal detection circuitry with a detachable connection; a first signal line configured to couple biometric signals from a first skin electrode to a first input of the signal detection circuitry for measurement of the biometric signals; a second signal line configured to couple reference signals of the biometric signals to a second input of the signal detection circuitry; and an impedance circuitry coupled between the first signal line and the second signal line, wherein impedance of the impedance circuitry is higher on a first frequency band covering a frequency band of the measured biometric signals than on a second frequency band outside the frequency band of the measured biometric signals.

Embodiments of the invention are defined in the dependent claims.

According to another aspect, there is provided an apparatus comprising: a first signal line configured to couple signals from a first skin electrode to a first input of a differential amplifier comprised as a front-stage in a signal detection circuitry for measurement of biometric signals sensed by the first skin electrode; a second signal line configured to couple signals from a second skin electrode, different from the first skin electrode, to a second input of the differential amplifier of the signal detection circuitry for measurement of biometric signals sensed by the second skin electrode; and an impedance circuitry coupled between the first signal line and the second signal line in order to tune input impedance of the differential amplifier, wherein impedance of the impedance circuitry is higher on a first frequency band covering a frequency band of the measured biometric signals than on a second frequency band outside the frequency band of the measured biometric signals.

BRIEF DESCRIPTION OF THE DRAWINGS

Embodiments of the present invention are described below, by way of example only, with reference to the accompanying drawings, in which FIG. 1 illustrates embodiments of measurement apparatuses for measuring biometric signals from a human body;

FIG. 2 illustrates an equivalent circuit diagram modeling an operating environment of biometric signal measurement;

FIG. 3 illustrates a block diagram of a measurement apparatus according to an embodiment of the invention;

FIG. 9 illustrates a circuit diagram of another interference suppression circuitry comprised in a measurement apparatus according to another embodiment of the invention;

FIG. 10 illustrates a circuit diagram of a controller comprised in FIGS. 8 and 9;

FIG. 11 illustrates an embodiment of a circuit diagram for a switch used in the interference suppression circuitry according to an embodiment of the invention;

FIGS. 18 to 20 illustrate embodiments of apparatuses comprising the interference suppression circuitry according to some embodiments of the invention.

DETAILED DESCRIPTION

Figure 4:
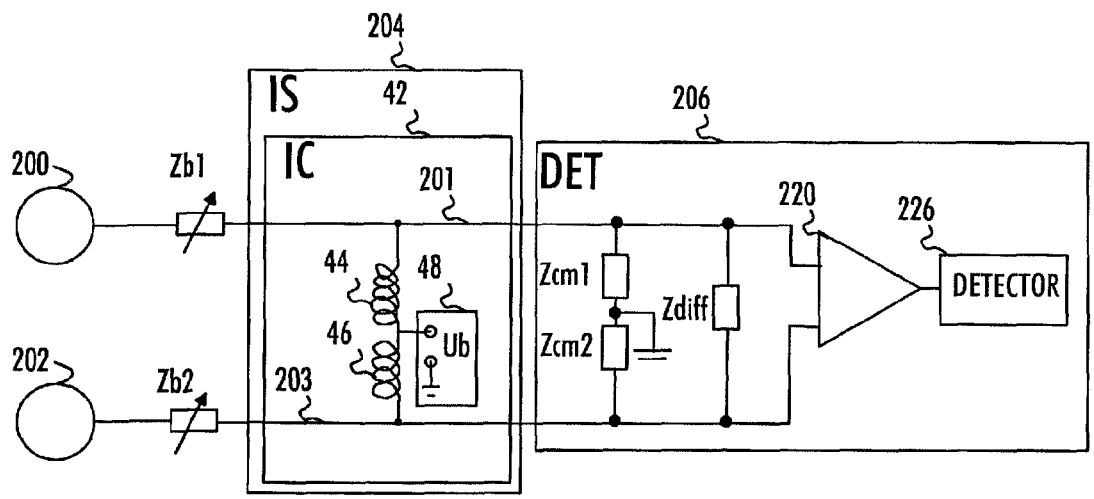
FIG. 4 illustrates a circuit diagram of an interference suppression circuitry comprised in a measurement apparatus according to an embodiment of the invention.

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Embodiments described herein relate to a measurement apparatus or a measurement system configured to measure biometric signals. In an embodiment, the measurement apparatus is configured to measure a heart activity signal of a subject. The heart activity signal comprises electrocardiograph (EKG) or a part thereof, such as P, Q, R, S, or T waves.

In an embodiment, the measurement apparatus is configured to measure muscle activity with a electromyography (EMG).

The subject may be a human or an animal body. Referring to FIG. 1, the measurement apparatus or the measurement system may comprise a plurality of skin electrodes 100 to 108 configured to be placed into physical contact with the skin of the body in order to carry out the measurement of the biometric signal. The skin electrodes 100 to 108 may be attached to various locations in the body, e.g. chest, shoulder(s), arm(s), wrist(s), and leg(s).

A skin electrode 100 to 108 is coupled to a measurement circuitry 110, which is exemplified with a heart rate transmitter 110 in FIG. 1. The measurement circuitry 110 receives the biosignals from the skin electrode 100 to 108, as illustrated by dashed lines connecting the electrodes 100 to 108 and the heart rate transmitter 110, and subjects the biosignals to signal processing.

In an embodiment, the measurement circuitry 110 is connected to a strap designed to be attached around the chest of the human. The strap comprises skin electrodes 103A, 103B that are connected to the input terminals of the measurement circuitry 110 and are in contact with the skin in the chest area. The measurement circuitry 110 may be integrated into the strap or the measurement circuitry 110 may comprise connector so that the strap provides an electromechanical support for the measurement circuitry 110.

In an embodiment of the invention, at least one skin electrode 100 to 108 is integrated into an apparel, such as a shirt. The apparel may comprise conducting means, such as wires or flex structures, which enable transferring the biosignals from the skin electrode 100 to 108 to the measurement circuitry 110. The measurement circuitry itself may be located in an arbitrary location in the apparel, and it may be fixed to the apparel.

Let us now consider conventional measurement of biometric signals in a measurement apparatus. As mentioned in the Background section, the movement of the skin electrodes 100 to 108 interferes with the measurement, and FIG. 2 illustrates a circuit diagram accounting for the above-mentioned interference sources. FIG. 2 illustrates a first skin electrode 200 and a second skin electrode 202. A first signal line 201 from the first skin electrode 200 is applied to a first input of a differential amplifier 220 comprised in a signal detection circuitry 206, and a second signal line 203 from the second skin electrode 202 is applied to a second input of the differential amplifier 220. The differential amplifier 220 may operate as a front stage of the signal detection circuitry, e.g. as a first operational component counted from an input of the signal detection circuitry and carrying out pre-processing of received signals, and amplify the received biosignals differentially and apply the amplified biosignal to a detector 226 configured to detect a determined waveform in the differentially amplified biosignal, e.g. one or more of the above-mentioned P, Q, R, S, and T waves. It should be noted that while the embodiments described below relate to a measurement apparatus comprising two skin electrodes 200, 202, the measurement apparatus may comprise more than two skin electrodes 100 to 108 or a single skin electrode 200 or 202. In the case of a single skin electrode 200 or 202, a reference signal may be provided to another input of the differential amplifier 220 by connecting the other input to a reference voltage source or to the ground, for example. The reference signal, such as the ground level, may be taken outside the subject being measured, e.g. outside the human skin.

In another embodiment, the reference signal is taken from an external equipment external to the measurement apparatus. The external equipment may be connected to the measurement apparatus and to the skin of the measured subject. Such an external equipment may be a larger system, such as a car or a treadmill having a biosignal measurement capability.

Referring to FIG. 2, the first signal line 201 comprises impedance $Z_{B1}$ in series between the first skin electrode 200 and the differential amplifier 220. Similarly, the second signal line 203 comprises impedance $Z_{B2}$ in series between the second skin electrode 202 and the differential amplifier 220. These impedances $Z_{B1}$ and $Z_{B2}$ are presented for the sake of illustrating the impedance between the skin electrode 200 or 202 and the human skin. Because of the motion of the skin electrodes 200, 202 with respect to the skin, the contact between the skin electrodes 200, 202 and the skin varies in time which results in time variance in the impedance values $Z_{B1}$ and $Z_{B2}$. The skin electrodes 200, 202 may move differently from each other and, thus the impedances $Z_{B1}$ and $Z_{B2}$ also vary with respect to each other. This may cause both common mode and differential interference to the measurements. In other words, the motion between the skin and skin electrodes modulates the impedances $Z_{B1}$ and $Z_{B2}$, thereby modulating interference degrading the performance of the measurements of the biosignal. Common mode impedances $Z_{cm1}$ and $Z_{cm2}$ that are arranged in series with respect to each other and between the first and second signal lines 201, 203, as illustrated in FIG. 2, represent a common mode input impedance of the signal detection circuitry 206. A ground may be applied between the common mode impedances $Z_{cm1}$, $Z_{cm2}$. Differential impedance $Z_{diff}$ arranged between the first and second signal lines 201, 203 as illustrated in FIG. 2 simulates the differential impedance of the signal detection circuitry 206. Additional differential impedance may be caused by non-idealities in component values between the common mode impedances $Z_{cm1}$ and $Z_{cm2}$. Voltages U1 and U2 represent voltages input to the differential amplifier 220 for differential amplification. From the circuit diagram of FIG. 2, it is possible to derive an equation for the voltages U1 and U2 as:

$$U1 = \frac{Z_{cm1} \| (Z_{diff} + Z_{cm2} \| Z_{B2})}{Z_{B1} + Z_{cm1} \| (Z_{diff} + Z_{cm2} \| Z_{B2})} \cdot [U_{EKG} + U_{cm}] \quad (1)$$

$$U2 = \frac{Z_{cm2} \| (Z_{diff} + Z_{cm1} \| Z_{B1})}{Z_{B2} + Z_{cm2} \| (Z_{diff} + Z_{cm1} \| Z_{B1})} \cdot [U_{EKG} + U_{cm}],$$

wherein $\|$ represents parallel connection of impedances. $U_{EKG}$ represents the biometric signal sensed from the human skin by the respective skin electrodes 200, 202, and $U_{cm}$ represents common mode interference signal that represent signals other than the desired biometric signal. The common mode interference signal represents signals that are induced to both signal lines 201, 203 similarly. As mentioned above, because of the motion between the skin electrodes 200, 202 and the skin (or more generally a surface to which the skin electrodes 200, 202 are connected), impedances $Z_{b1}$ and $Z_{b2}$ are a function of motion as:

$$Z_{B1} = Z_{B1}(m)$$

$$Z_{B2} = Z_{B2}(m) \quad (2)$$

One could also say that they are a function of time instead of motion, and the analysis is the same in that case, because the aim is to eliminate the time variability in the impedance. In order to eliminate the interference caused by the motion of the skin electrodes 200, 202, the voltages U1 and U2 should be constant over motion of the skin electrodes 200, 202 as:

$$\frac{\partial U_1}{\partial m} = 0 \quad (3)$$

$$\frac{\partial U_2}{\partial m} = 0$$

When looking at Equation (1), the combined impedance should be as constant as possible, and this may be achieved in two cases:

$$Z_{cm1} \ll \{Z_{B1}, Z_{B2}\} \text{ and } Z_{cm2} \ll \{Z_{B1}, Z_{B2}\} \quad 1)$$

$$Z_{cm1} \gg \{Z_{B1}, Z_{B2}\}; Z_{cm2} \gg \{Z_{B1}, Z_{B2}\}; \text{ and}$$
$$Z_{diff} \gg \{Z_{B1}, Z_{B2}\}. \quad 2)$$

Let us first consider case 1). If the common mode impedances $Z_{cm1}$ and $Z_{cm2}$ are much lower than the impedances $Z_{B1}$ and $Z_{B2}$ representing the skin-electrode interface, the numerator becomes almost zero (or a very low value for both U1 and U2.

Referring to FIG. 2, the common mode impedances $Z_{cm1}$ and $Z_{cm2}$ effectively ground the skin electrodes 200, 202 to each other in such a case. As a consequence, the interference caused by the motion of the skin electrodes 200, 202 is diminished but so is the biometric signal $U_{EKG}$ that is to be measured, resulting in zero (or low) values for U1 and U2, which is not desirable. Therefore, case 1) may be discarded.

With respect to case 2), the input impedances of the differential amplifier 220, i.e. the common mode impedances $Z_{cm1}$ and $Z_{cm2}$ and the differential impedance $Z_{diff}$, are much higher than the impedances $Z_{B1}$ and $Z_{B2}$ representing the skin-electrode interface. As a consequence, with some approximation, both numerator and denominator of the impedance of U1 becomes $Z_{cm1} \| Z_{diff}$ which makes the total impedance approximately constant. The similar effect occurs with respect to U2. As the input impedance of the signal detection circuitry 206 becomes roughly constant whenever the input impedance of the signal detection circuitry 206 is significantly higher than the impedances $Z_{B1}$ and $Z_{B2}$, the contribution of the impedances $Z_{B1}$ an $Z_{B2}$ becomes insignificant, and the interference caused by the motion of the skin electrodes 200, 202 is suppressed.

Additionally, the human body contains numerous electric charges all around the human body. These electric charges are conducted to the skin electrodes 100 to 108, 200, 202 together with the measured biometric signal, and such electric charges may also modulate the impedances $Z_{B1}$ and $Z_{B2}$ in FIG. 2 as a function of the motion of the skin electrodes with respect to the measurement surface, such as the human skin. The total electric charge of the human body may be represented by a DC voltage source connected between the skin electrodes 100 to 108, 200, 202. Accordingly, the following equation may be derived for a voltage difference U1−U2:

$$U1 - U2 = \frac{Z_{diff} \| (Z_{cm1} + Z_{cm2})}{Z_{B1} + Z_{B2} + Z_{diff} \| (Z_{cm1} + Z_{cm2})} \cdot U_N, \quad (4)$$

where $U_N$ represents the DC voltage caused by the electric charges of the human body. As the impedances $Z_{B1}$ and $Z_{B2}$ are also modulated as the function of the motion in this case, Equation (2) applies, and in order to eliminate the interference, U1−U2 should be constant as the function of the motion, that is:

$$\frac{\partial (U_1 - U_2)}{\partial m} = 0 \quad (5)$$

This is realized in the following three cases:

$$Z_{diff} = 0 \text{ and/or } Z_{cm1} = Z_{cm2} = 0 \quad 3)$$

$$Z_{cm1} \gg \{Z_{B1}, Z_{B2}\}, Z_{cm2} \gg \{Z_{B1}, Z_{B2}\}; \text{ and}$$
$$Z_{diff} \gg \{Z_{B1}, Z_{B2}\} \quad 4)$$

$$U_N = 0 \quad 5)$$

Let us first consider case 3). When the impedances are set to zero, the interference is suppressed, but so is the desired signal because the skin electrodes 200, 202 are grounded to each other. With respect to case 4), when the input impedance of signal detection circuitry 206 is set to be much higher than the impedances $Z_{B1}$ and $Z_{B2}$, the interference is mitigated. With respect to case 5), if the electric charges are non-existent, there is no interference to be suppressed. While this may not be a practical scenario, let us still select it for further study along with cases 2) and 4) when deriving an interference suppression circuitry that mitigates the interference caused by the motion of the skin electrodes 100 to 108, 200, 202.

FIG. 3 illustrates a general block diagram of the measurement apparatus according to an embodiment of the invention. The measurement apparatus comprises the first skin electrode 200 and the second skin electrode 202 that are designed to sense bodily currents in the body of the subject and forward them as electrical signals. i.e. biosignals, in the measurement apparatus. The measurement apparatus further comprises an interference suppression circuitry 204 configured to suppress the interference caused by the motion of the skin electrodes 200, 202. The interference suppression circuitry 204 is an apparatus that comprises a first signal line 201, configured to couple biosignals from the first skin electrode 200 to the signal detection circuitry 206 for measurement of biometric signals sensed by the first skin electrode 200. The apparatus further comprises a second signal line 203 configured to couple signals from the second skin electrode 202 to the signal detection circuitry 206 for measurement of biometric signals sensed by the second skin electrode 202. Embodiments of the circuit diagram of the interference suppression circuitry 204 are described in greater detail below.

The signal detection circuitry 206 is configured to detect signals sensed by the first and the second skin electrodes 200, 202. In an embodiment, the signal detection circuitry 206 is configured to detect a determined waveform in the biometric signal(s) received from the skin electrodes 100 to 108, 200, 202. The detected waveform may then be used to compute various parameters of the biometric signal, e.g. electrocardioghraphic characteristics, such as ECG waveform, P, Q, R, S, T waves, the heart rate or heart rate variability, for example. The measurement apparatus may further comprise a communication circuitry 208 configured to transmit the measured biometric signals and/or any other biometric information obtained from the measurement to an external receiver apparatus. The communication circuitry 208 may comprise a wireless communication circuitry and/or a wired communication circuitry, and the biometric information may be transmitted through the communication circuitry in order to display the biometric information through a user interface.

When implementing the interference suppression circuitry 204, let us consider the selected cases 2), 4), and 5) that set conditions to the input impedance of the signal detection circuitry 206. From cases 2), 4), and 5), we obtain the following frequency-dependent conditions for the input impedance:

$$2) \,\&\, 4): \begin{cases} Z_{diff} \to \infty \\ Z_{cm1} \to \infty, f = f_{MEAS} \\ Z_{cm2} \to \infty \end{cases} \quad (6)$$

$$5) \begin{cases} Z_{diff} \to 0 \\ Z_{cm1} \to 0, f = 0 \\ Z_{cm2} \to 0 \end{cases}$$

With respect to conditions 2) and 4), when the input impedance approaches infinity (or has a very high value) on a measurement band $f_{MEAS}$, the interference in the form of the impedance modulation caused by the motion of the skin electrodes 200, 202 does not affect the measurement. On the other hand, the input impedance should approach zero on DC (zero frequency), thereby releasing the electrical DC charges of the human body to the ground, thereby eliminating their effect on the measurement. In order to satisfy the conditions of Equation (6), embodiments of the invention provide, as the interference suppression circuitry 204, an impedance circuitry coupled between the first signal line 201 and the second signal line 203. The impedance circuitry may be understood as an additional frequency-dependent impedance that is connected to an input of the signal detection circuitry 206 and the differential amplifier 220. The impedance of the impedance circuitry is higher on a first frequency band covering a frequency band of the measured biometric signals than on a second frequency band outside the frequency band of the measured biometric signals. The second frequency band may include the DC. The differential amplifier 220 may have nominal input impedance, and the impedance circuitry may be used as an additional impedance before the differential amplifier 220 so as to eliminate (or at least suppress or mitigate) the interference before the differential amplifier 220. FIG. 4 illustrates an embodiment of such an interference suppression circuitry 204. Referring to FIG. 4, the interference suppression circuitry 204 comprises the above-mentioned impedance circuitry denoted by numeral 42 and comprising at least a first and a second impedance component 44 and 46 that are connected between the first and the second signal line 201, 203, thereby connecting the first and second skin electrode 200, 202 to each other before the signal detection circuitry 206 and the differential amplifier 220. In more detail, a first terminal of the impedance circuitry 42 is connected to the first signal line 201, and a second terminal of the impedance circuitry 42 is connected to the second signal line 203. Each impedance component 44, 46 may be formed by a sub-circuitry realizing a circuitry equivalent to a high inductance. The impedance circuitry 42 may comprise a first sub-circuitry, e.g. the first impedance component 44, and a second sub-circuitry, e.g. the second impedance component 46. A first terminal of the first sub-circuitry 44 is connected to the first signal line 201, a second terminal of the first sub-circuitry 44 is connected to a first terminal of the second sub-circuitry. Furthermore, a second terminal of the second sub-circuitry 46 is connected to the second signal line 203, and the second terminal of the first sub-circuitry 44 and the first terminal of the second sub-circuitry 46 are connected to a bias voltage supply circuitry 48 configured to provide an input bias voltage Ub for the differential amplifier 220. The bias voltage supply circuitry 48 may be included in the interference suppression circuitry 204, or it may be external to the interference suppression circuitry 204.

Figure 5:
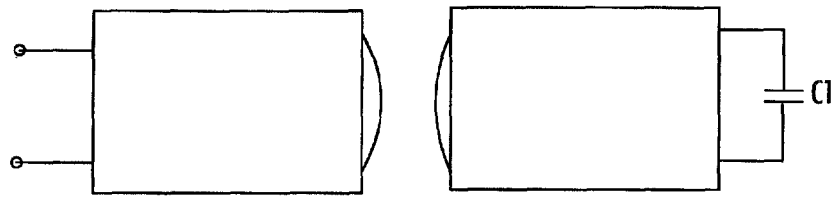
FIG. 5 illustrates a circuit diagram of a component comprised in the interference suppression circuitry according to an embodiment of the invention.
Figure 6:
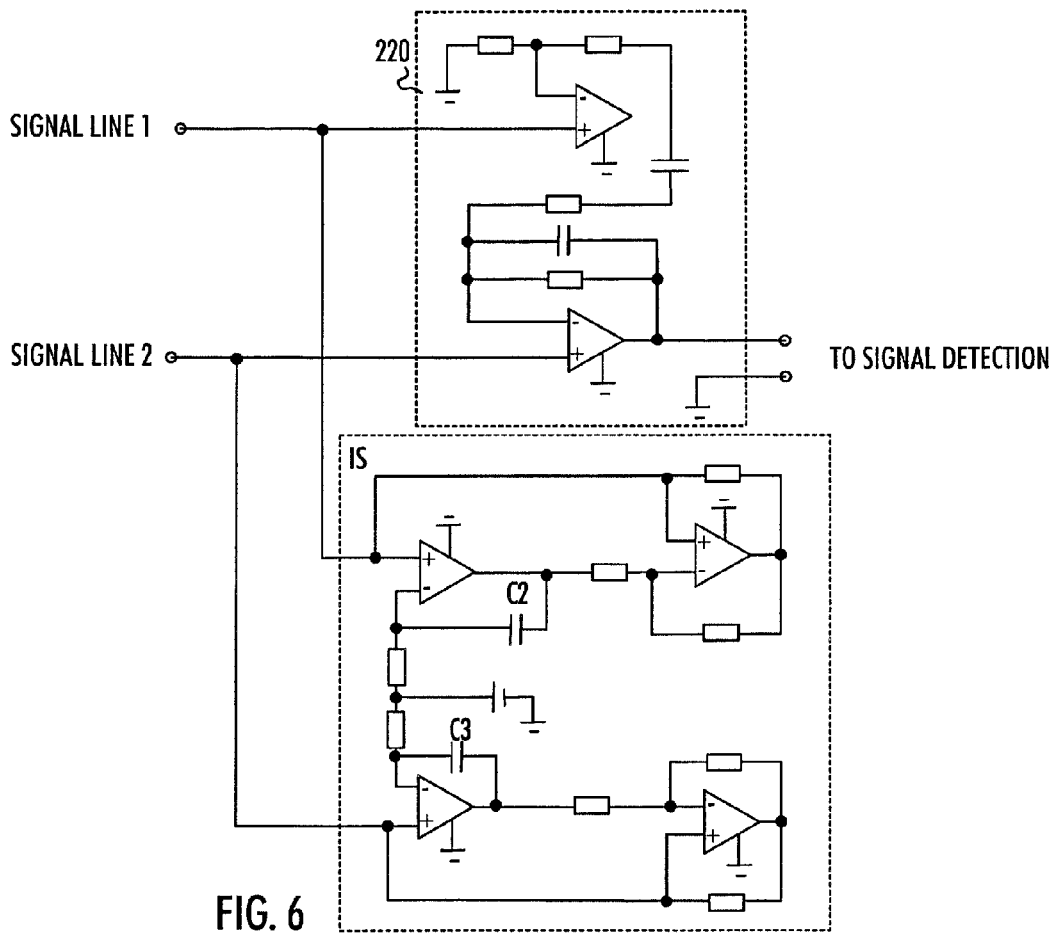
FIG. 6 illustrates a detailed circuit diagram of an interference suppression circuitry comprised in a measurement apparatus according to an embodiment of the invention.

In an embodiment, each impedance component 44, 46 is realized by a gyrator circuitry such as the one shown in FIG. 5. The gyrator of FIG. 5 effectively transforms the capacitor C1 to function as an inductor. FIG. 6 illustrates an embodiment of a detailed circuit diagram of the interference suppression circuitry formed by two gyrators transforming the capacitors C2, C3 into inductors. FIG. 6 illustrates also an embodiment of the circuit diagram of the differential amplifier 220. In order to realize an adaptive impedance circuitry 42, the impedance circuitry 42 may comprise a plurality of impedance components arranged in parallel and a switch circuitry arranged to connect and disconnect selectively each impedance component to/from the impedance circuitry 42. For example, in the embodiments of FIGS. 5 and 6, a plurality of capacitors may be arranged in parallel such that one or more capacitors may be selectively connected to the gyrator by closing/opening selection switches appropriately. This enables to tune the impedance circuit and the measurement apparatus for different measurement scenarios. A signal closing the switches may be provided by a controller according to a selected measurement mode. The selected measurement mode may be received by the controller as a command from a user through a user interface or through the communication circuitry of the measurement apparatus. In another evaluation, the controller may be configured to monitor the performance of the measurement and/or a quality of the measured signal, e.g. a signal-to-noise ratio (SNR). When the performance or the SNR degrades, the controller may tune the input impedance according to a determined criterion.

Figure 7:
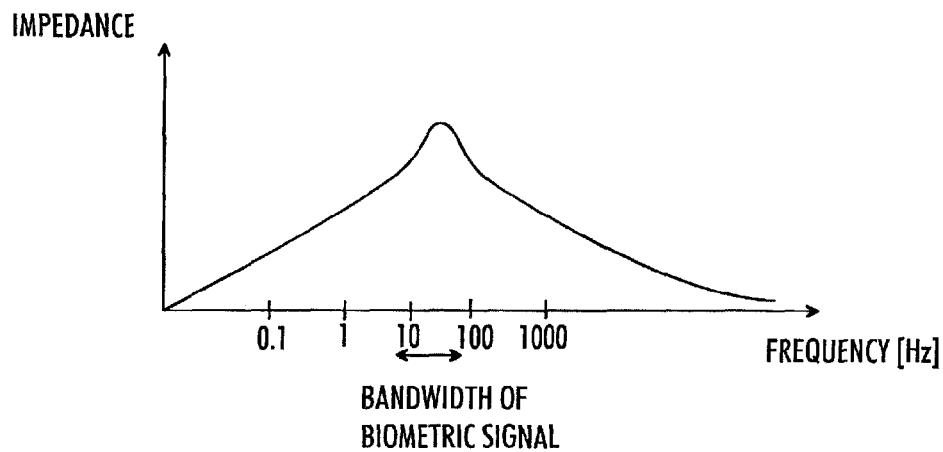
FIG. 7 illustrates an impedance graph of an impedance circuit according to an embodiment of the invention.

FIG. 7 illustrates the frequency-dependent input impedance of the interference suppression circuitry 204 according to an embodiment of the invention. Let us assume that the measured biometric signal is a heart activity signal located on a frequency band around 10 to 80 Hz. As shown in FIG. 7, the input impedance of the interference suppression circuitry 204 is higher on that frequency band (forming the measurement band) than outside the measurement band. The low input impedance of the interference suppression circuitry 204 below the measurement band is inherently caused by the inductance which operates as a short circuit on the DC frequency and as infinite impedance on infinite frequency. With suitable selection of component values for the resistors and the capacitors included in the interference suppression circuitry 204, the interference suppression circuitry 204 may be configured to tune the input impedance such that the input impedance of the interference suppression circuitry 204 decreases also above the measurement band.

Let us assume that the measured biometric signal is a heart activity signal and that the signal detection circuitry 206 is configured to detect a QRS complex from the heart activity signal sensed from the subject to which the skin electrodes 100 to 108, 200, 202 are attached. In such a case, the interference suppression circuitry 204 may be configured to provide frequency-dependent impedance on the frequency band of the QRS signal as follows:

10 to 20 Hz: any one of 100 to 300 kilo-ohms, 300 to 1000 kilo-ohms, 1 to 3 Mega ohms, and 3 to 10 Mega ohms; and 20 to 50 Hz: any one of 100 to 300 kilo-ohms, 300 to 1000 kilo-ohms, 1 to 3 Mega ohms, and 3 to 10 Mega ohms.

The interference suppression circuitry 204 may be configured to provide frequency-dependent impedance outside the frequency band of the QRS signal as follows:

0 to 1 Hz: any one of 0 to 100 ohms, 100 to 300 ohms, 300 to 1000 ohms, 1 to 3 kilo-ohms, 3 to 10 kilo-ohms, 10 to 30 kilo-ohms, 30 to 100 kilo-ohms;

1 to 3 Hz: any one of 0 to 100 ohms, 100 to 300 ohms, 300 to 1000 ohms, 1 to 3 kilo-ohms, 3 to 10 kilo-ohms, 10 to 30 kilo-ohms, 30 to 100 kilo-ohms;

3 to 10 Hz: any one of 0 to 100 ohms, 100 to 300 ohms, 300 to 1000 ohms, 1 to 3 kilo-ohms, 3 to 10 kilo-ohms, 10 to 30 kilo-ohms, 30 to 100 kilo-ohms; and above 100 Hz: any one of 0 to 100 ohms, 100 to 300 ohms, 300 to 1000 ohms, 1 to 3 kilo-ohms, 3 to 10 kilo-ohms, 10 to 30 kilo-ohms, 30 to 100 kilo-ohms.

With respect to the triboelectric effect that causes the skin electrodes attached to different locations in the subject to be in different electric potentials, an embodiment of the present invention provides a coupling circuitry 207 disposed between the first signal line 201 and the second signal line 203 to equalize the potentials, i.e. to eliminate the potential difference. The coupling circuitry 207 may be used to improve the performance of the above-described interference suppression circuitry 204 by eliminating the triboelectric effect.

Figure 8:
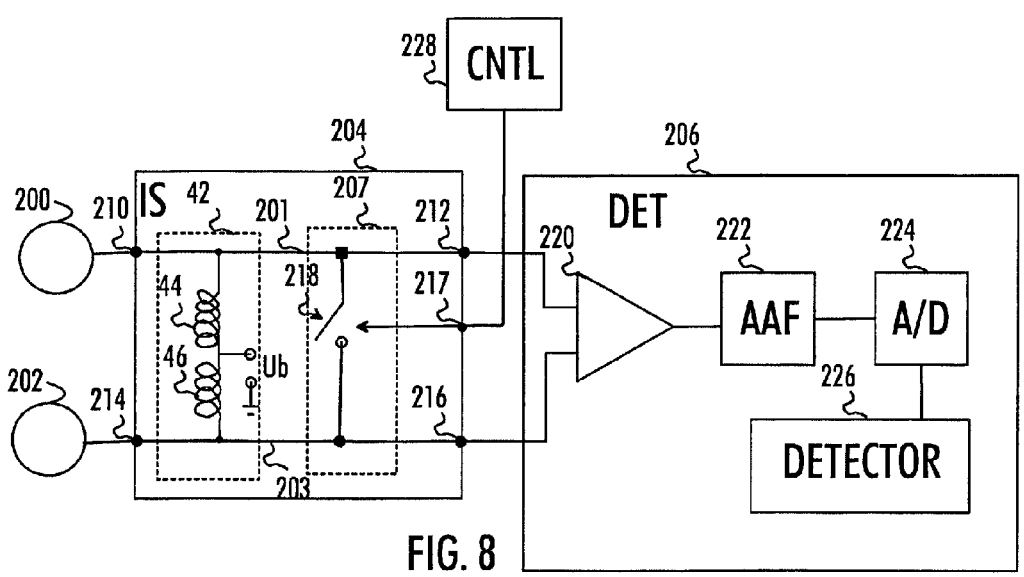
FIG. 8 illustrates a circuit diagram of an interference suppression circuitry comprised in a measurement apparatus according to another embodiment of the invention.

FIG. 8 illustrates an embodiment of the interference suppression circuitry 204. The interference suppression circuitry 204 comprises a first input terminal 210 connected to the first skin electrode 200, and a second input terminal 214 connected to the second skin electrode 202. The interference suppression circuitry 204 further comprises a first output terminal 212 connected to the first input terminal 210, and a second output terminal 216 connected to the second input terminal 214. The output terminals 212 and 216 are further connected to respective input terminals of an input interface of the signal detection circuitry 206.

The interference suppression circuitry 204 comprises the impedance circuitry 42 comprising the impedance components 44 and 46 disposed between the signal lines 201, 203.

The interference suppression circuitry 204 further comprises the coupling circuitry 207 according to an embodiment of the invention. In some embodiments, the coupling circuitry 207 forms the interference suppression circuitry 204 together with the impedance circuitry 42, while in other embodiments the interference suppression circuitry 204 comprises additional components. The coupling circuitry 207 is in this embodiment arranged to comprise a switch 218 that is responsive to a control signal external to the interference suppression circuitry 204, wherein the control signal selectively closes and opens the switch 218. The interference suppression circuitry 204 may further comprise a third input terminal 217 for receiving the control signal from a controller 228 that is conveyed to the switch 218. A first terminal of the switch 218 may be connected to the first signal line 201 comprising the first input terminal 210 and the first output terminal 212, and a second terminal of the switch 218 may be connected to the second signal line 203 comprising the second input terminal 214 and the second output terminal 216. The signal lines needed to connect the switch 218 to the signal lines 201, 203 may be comprised in the coupling circuitry. In operation, the switch 218 selectively couples, e.g. short circuits, the first signal line 201 to the second signal line 203 in response to the control signal. As a consequence, the potential difference between the first and the second skin electrode 200, 202 is equalized, and the equalization is carried out before the signal detection circuitry 206.

In an embodiment, the input terminals 210, 214 and the output terminals 212, 216 may be logical terminals or both logical and physical terminals. For example, when the skin electrodes 200, 202 are detachable from the interference suppression circuitry 204, connectors connecting and disconnecting the skin electrodes 200, 202 to/from the interference suppression circuitry 204 may be provided in which case such connectors may be construed to form the input terminals 210, 214.

In an embodiment, the skin electrodes 200, 202 are integrated into the interference suppression circuitry 204, and a single continuous signal line with no connectors may be provided from the skin electrodes 200, 202 to the outputs of the interference suppression circuitry 204. Similarly for the output terminals 212, 216, if the signal detection circuitry 206 is detachable from the interference suppression circuitry 204, connectors connecting and disconnecting the skin electrodes 200, 202 to/from the interference suppression circuitry 204 may be provided in which case such connectors may be construed to form the output terminals 212, 216.

In an embodiment, the interference suppression circuitry 204 is integrated with the signal detection circuitry 206, and a single continuous signal line with no connectors may be provided from the respective input terminals to the input of the signal detection circuitry 206. As a consequence, a single signal line may be provided from each skin electrode 200, 202 to the input of the signal detection circuitry 206, and no physical terminals may be provided in the interference suppression circuitry 204, except optionally for the control signal controlling the switch 218.

The signal detection circuitry 206 may comprise an amplifier 220 configured to amplify the signal received through the first and second signal lines 201, 203 from the respective skin electrodes 200, 202. The amplifier 220 may be a differential amplifier, and an impedance circuit (42) may be provided at the input of the amplifier 220 so as to tune the frequency contents of the biosignal directed to the input terminals of the signal detection circuitry 206. The signal detection circuitry 206 may further comprise an anti-aliasing filter 222 connected to an output of the amplifier 220 and configured to remove high frequency components that might cause aliasing in an analog-to-digital conversion. The anti-aliasing filter 222 may output a filtered and amplified signal to an analog-to-digital (A/D) converter 224 configured to sample the received (analog) signal and convert it into a digital signal. The digital signal may then be applied to a detector 226 that is arranged to detect determined events in the received signal, e.g. determined waveforms, peaks, etc.

In an embodiment, the detector 226 may be configured to operate in an analog domain and, accordingly, an input of the detector 226 may be connected to an output of the amplifier 220, and the anti-alias filtering and the A/D conversion may follow the detector 226, or they may even be omitted. Such a detector 226 operating in the analog domain may comprise a peak detector, for example.

It should be noted that while the embodiments described herein relate to a measurement apparatus comprising two skin electrodes 200, 202, the measurement apparatus may comprise a single skin electrode 200, and a reference signal may be provided to another input of the differential amplifier 220 by connecting the other input to a reference voltage source or to the ground, for example. In the embodiments described herein, one of the skin electrodes 200, 202 may be understood as a reference skin electrode providing the differential amplifier with the reference signal, e.g. a reference voltage, while the other skin electrode 200, 202 provides the measurement signal.

As described above, some embodiments of the invention provide the coupling circuitry 207 in the interference suppression circuitry 204 in order to equalize the electrical potential difference between the skin electrodes 200, 202. While FIG. 8 illustrates an embodiment of the interference suppression circuitry 204 that provides a simple, yet effective circuit configuration by short-circuiting the signal lines 201, 203, the signal lines 201, 203 may each be connected to a common, third potential.

FIGS. 9A, 9B, and 9C illustrate further embodiments of the interference suppression circuitry 204. FIG. 9A illustrates a circuit diagram of an embodiment, where both signal lines 201, 203 are connected separately to a common reference potential Vref that is not (necessarily) the potential of either skin electrode 200, 202. The reference potential Vref may be a potential or a voltage that is kept constant in the measurement apparatus comprising the interference suppression circuitry 400 according to this embodiment. The reference potential may be the ground, or it may be a non-zero potential.

Referring to FIG. 9A, the interference suppression circuitry 400 according to this embodiment comprises a first switch 402 having its one terminal connected to the first signal line 201 (connecting the first skin electrode 200 to the signal detection circuitry 206) and the other terminal connected to the reference potential Vref. The coupling circuitry further comprises a second switch 404 having its one terminal connected to the second signal line 203 (connecting the second skin electrode 202 to the signal detection circuitry 206) and the other terminal connected to the reference potential Vref. The switches 402, 404 may be opened and closed simultaneously or at different times by applying a control signal to the switches 402, 404 from the controller 228. As a consequence, the switches 402, 404 comprised in the coupling circuitry equalize, in response to the control signal, the potential difference between the skin electrodes 200, 202. In FIG. 9A, the components denoted by the same reference numerals as in FIGS. 2 and 3 may have the same structure and/or functionality, and the description of them is omitted for the sake of conciseness. The interference suppression circuitry may further comprise the impedance circuitry, as illustrated in FIG. 9A. In FIGS. 9B and 9C, the impedance circuitry is omitted for the sake of clarity, but it should be understood that the impedance circuitry may be provided in these embodiments as well.

FIG. 9B illustrates an embodiment of the coupling circuitry 410 that combines the embodiments of FIGS. 3 and 4A. Referring to FIG. 4B, the coupling circuitry 410 is formed between the first and second signal line 201, 203 to selectively couple the signal lines 201, 203 to each other and to a common reference potential Vref that is applied between the signal lines 201, 203. The coupling circuitry 410 comprises in this embodiment two switches: a first switch 412 coupled to the first signal line 201 and a second switch 414 coupled between the first switch 412 and the second signal line 203. The reference potential Vref is applied to a signal line between the switches 412, 414. The switches 412, 414 are selectively closed and opened according to the control signals provided by the controller 228. The controller 228 may be configured to apply the same control signal to both switches 412, 414, thereby closing and opening the switches 412 simultaneously and thus implementing the selective coupling of the signal lines 201, 203. The control signal may be a clock signal, and the clock signal with same properties (frequency and phase) may be applied to all switches 412, 414 of the coupling circuitry 410. The reference potential Vref may be a biasing voltage of the differential amplifier 220 in both embodiments of FIGS. 9A and 9B. Therefore, the reference potential Vref may be selected to provide a potential that is between operational voltages of the differential amplifier 220, thereby tuning the signal level according to a dynamic range of the differential amplifier 220.

FIG. 9C illustrates yet another embodiment, wherein the coupling circuitry 420 comprises further components. It should be appreciated that one or more other components may be included in the coupling circuitry, e.g. any one of the coupling circuitries of the embodiments of FIGS. 8, 9A, and 9B. Referring to FIG. 9C, this embodiment of the coupling circuitry 420 comprises at least one switch 422 carrying out the coupling of the signal lines 201, 203 to each other (or to a common potential). The coupling circuitry 420 further comprises, for example, a resistor 424 in series with the switch 422. The resistor may also represent internal resistance of the switch(es) comprised in the coupling circuitry 420. The resistor 424 may also include inherent reactive properties in the form of parasitic capacitance and inductance. Embodiments where additional components are included in the coupling circuitry 420 also reduce the potential difference between the skin electrodes 200, 202, although the embodiments may require a longer duration to equalize the potential difference between the skin electrodes 200, 202, depending on the properties of the components.

In the above-described embodiments, and generally in other embodiments, the number of skin electrodes 200, 202 is not limited to two, and the number of skin electrodes 200, 202 may be higher than two, e.g. three, four, etc. With respect to the embodiment of FIG. 8, the interference suppression circuitry 204 may be configured to couple the skin electrodes 200, 202 by short-circuiting them according to the control signal controlling the short-circuiting. One of the skin electrodes 200, 202 may be selected as a reference skin electrode, and the other skin electrodes 200, 202 may be connected to the reference skin electrode so as to equalize the potential difference, e.g. by adjusting the potential of the other skin electrodes to match with the potential of the reference skin electrode. Referring to FIGS. 9A, 9B and 9C, the reference potential Vref may be the potential of the reference skin electrode or it may be the fixed potential, as described above.

Let us now consider the control signal(s) and the controller 228 controlling the operation of the switches 218, 402, 404. Referring to FIG. 10, the controller 228 may comprise a clock signal generator 500 configured to generate a clock signal. The clock signal generator 500 may be a square wave oscillator, for example. The clock signal generated by the clock signal generator 500 may be output to a control logic circuitry 502 configured to modify the clock signal to produce the control signal(s) applied to the switches 218, 402, 404. The control logic circuitry 502 may be configured to modify the input clock signal into a plurality of clock signal(s) and, optionally, adjust properties of the clock signals. The control logic circuitry 502 may be configured to modify at least one of the phase and duty cycle of the clock signals to produce the control signal(s).

In an embodiment, the control logic circuitry 502 is configured to output a plurality of output clock signals, wherein at least one of the output clock signals is applied to the switch(es) 218, 402, 404 (depending on the circuit and number of switches in the interference suppression circuitry 204, 400, 410, 420), and at least one of the output clock signals is applied to another component of the apparatus, e.g. the A/D converter 224. The control logic circuitry 502 may be configured to modify the clock signals such that the clock signals applied to the switches, e.g. switches 402, 404, are identical. This controls the plurality of switches to open and close simultaneously. In another embodiment, the control logic circuitry 502 is be configured to modify the clock signals such that the clock signals applied to the switches, e.g. switches 402, 404, are not identical. Accordingly, the different switches 402, 404 may be connected to the reference potential Vref alternately. In an embodiment, the control logic circuitry 500 is configured to modify the clock signals applied to the switch(es) such that they differ from clock the signal(s) applied to the other component(s) in at least one of the phase and the duty cycle. This may be used to control that the switch(es) 218, 402, 404 are not closed at a sampling instant of the A/D converter 224. This is discussed in greater detail with reference to timing diagrams of FIGS. 12 to 14.

FIG. 11 illustrates an embodiment of a switch which may constitute any one of the switches 218, 402, 404. In this embodiment, the switch is formed by two bipolar transistors arranged as illustrated in FIG. 11. A signal Vdrive applied to bases of the two transistors is the above-mentioned clock signal, and Vbias refers to a bias voltage. Terminals of the switches may be connected to at least one of the signal lines 201, 203 of the interference suppression circuitry, as described above in connection with FIGS. 8 and 9A to 9C. It should be appreciated that instead of the bipolar transistors, field effect transistors may be used to realize the switches 218, 402, 404.

Figure 12:
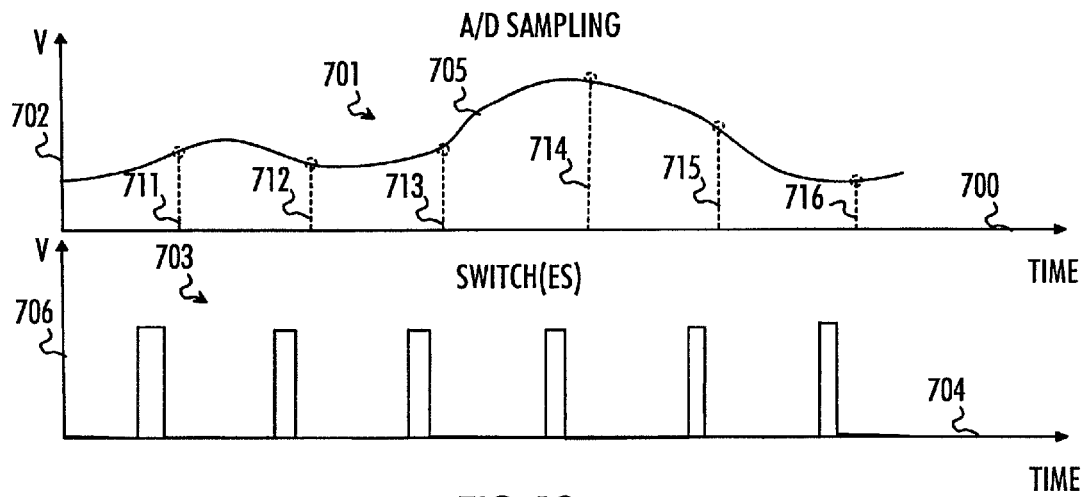
FIGS. 12 to 14 illustrate embodiments for timing the operation of the interference suppression circuitry according to some embodiments of the invention.
Figure 13:
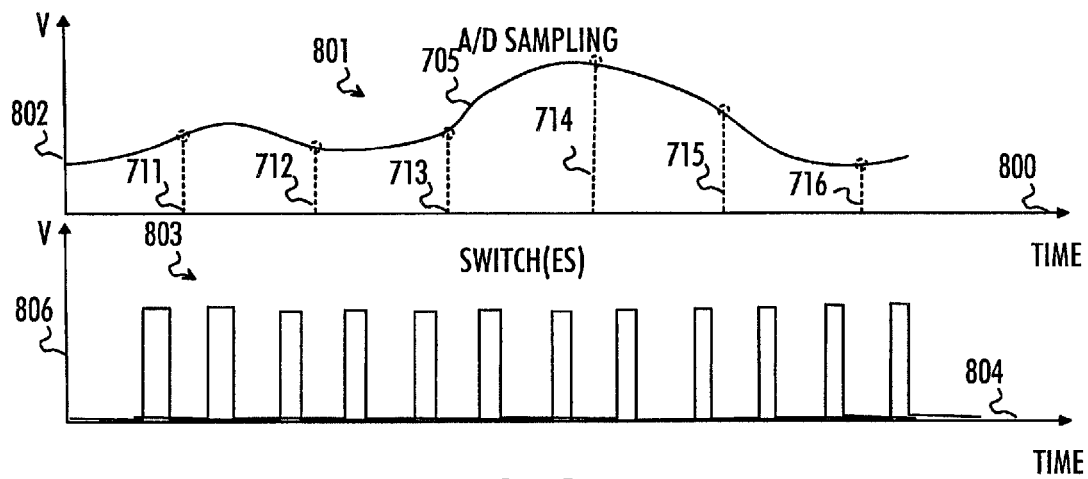
Figure 14:
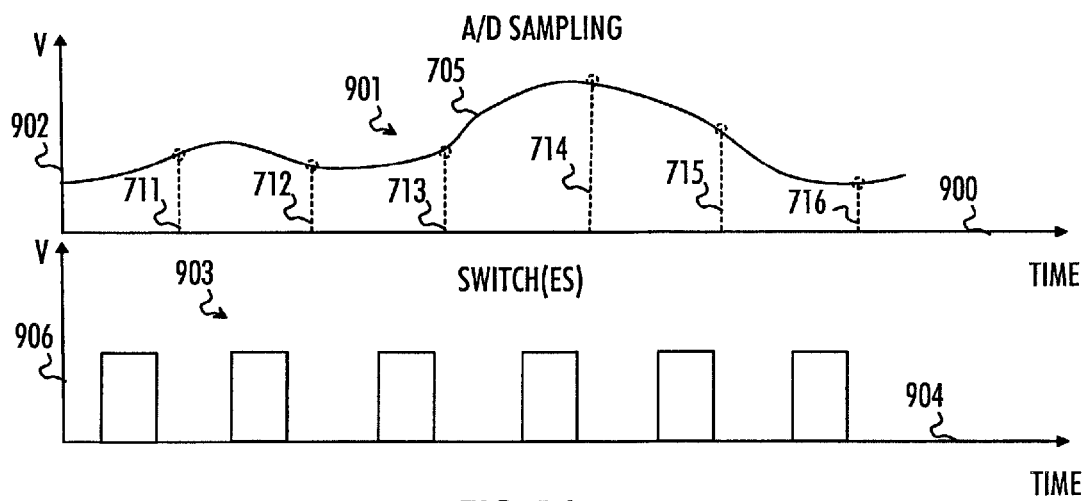

Let us now consider embodiments for controlling the operation of the switches with respect to a sampling instant of the A/D converter 224 configured to A/D convert the signal received from the skin electrodes. FIGS. 7 to 9 illustrate such embodiments. In each FIGS. 12 to 14, two graphs are illustrated. A horizontal axis 700, 704, 800, 804, 900, 904 denotes time, and a vertical axis 702, 706, 802, 806, 902, 906 denotes voltage or amplitude. A topmost graph 701, 801, 901 in each Figure illustrates as a solid, continuous line 705 an analog signal received by the A/D converter 224 and sampling instants of the A/D converter 224 as vertical dashed lines with dots 711 to 716 marking samples acquired by the A/D converter 224. Let us note that the signal illustrated in FIGS. 12 to 14 is an arbitrary signal and, in practice, the signal may be the biometric signal (e.g. a heart activity signal) sensed by the skin electrodes 200, 202. The lower graph 703, 803, 903 in each FIGS. 12 to 14 illustrates time intervals when the switches 218, 402, 404 of the interference suppression circuitry 204 are open and closed. The signal illustrated in the lower graphs 703, 803, 903 is the clock signal controlling the switches 218, 204, 404. When the clock signal is HIGH (has a higher voltage/amplitude), the switches 218, 402, 404 are closed and conduct current, and when the clock signal is LOW (has a lower voltage/amplitude), the switches 218, 402, 404 are open and do not conduct current. It should be understood that the switches 218, 402, 404 may also be configured to open when the clock signal is HIGH and to close when the clock signal is LOW, depending on the implementation of the switches 218, 402, 404.

Referring to FIG. 12, the switches 218, 402, 404 are closed and the potential difference between the skin electrodes 200, 202 is equalized between sampling instants of the A/D converter 224. As a consequence, the interference caused by the potential difference is suppressed between the sampling instants, and the interference does not propagate to the A/D conversion. In this embodiment, the frequency of the clock signal closing the switches 218, 402, 404 is the same as the frequency of the sampling instants of the A/D converter 224. However, in other embodiments where the interference is lower, the frequency of the sampling instants of the A/D converter 224 is a multiple (higher than one) of the frequency of the clock signal closing the switches 218, 402, 404. In such a case, the interference suppression is carried out less frequently, and there may be a plurality of consecutive sampling instants with no interference suppression interval between them. On the other hand, the frequency of the clock signal may be a multiple (higher than one) of the frequency of the sampling instants of the A/D converter 224 and, thus, a plurality of interference suppression intervals may be provided between the sampling instants, as illustrated in FIG. 13. FIG. 14 illustrates an embodiment where the duty cycle of the clock signal controlling the switches is higher than in FIGS. 12 and 13. In other words, the clock signal is HIGH for a longer time interval than in the embodiments of FIGS. 12 and 13 and, as a consequence, the switches 218, 402, 404 are closed for a longer duration. In an embodiment, the duration when the switches 218, 402, 404 are closed at a time is longer than the duration when the switches 218, 402, 404 are open so that the interference suppression interval is longer than a time interval between consecutive interference suppression intervals. The sampling instant may still be configured to be provided between the interference suppression intervals.

In all embodiments of FIGS. 12 to 14, an interference suppression interval is provided just before the sampling instant. Therefore, according to some embodiments, the interference suppression circuitry 204 is configured to couple the skin electrodes 200, 202 to the common potential during a latter half of a time interval between consecutive sampling instants of the analog-to-digital converter. Such embodiments reduce the amount of potential difference that may be generated in the skin electrodes 200, 202 before a given sampling instant.

The switches 218, 402, 404 driven by the clock signal also operate as a frequency mixer, thereby resulting in a signal that has intermodulation distortion. In order to separate frequency components caused by the intermodulation, the frequency of the clock signal may be selected to be higher than a highest frequency component of the measured biometric signal. For example, the highest frequency component of a heart activity signal is less than 100 Hz and, thus, the frequency of the clock signal may be higher than 100 Hz, e.g. between 100 and 500 Hz. As a consequence, a filter located between the interference circuitry and the detector, e.g. the anti-aliasing filter 222, may be configured to have a pass-band that excises intermodulation components to avoid aliasing in the A/D conversion and/or interference in the detection.

In an embodiment, the frequency of the clock signal functioning as the control signal is more than 500 Hz.

In an embodiment, the frequency of the clock signal functioning as the control signal is between 10 and 100 Hz.

Figure 15:
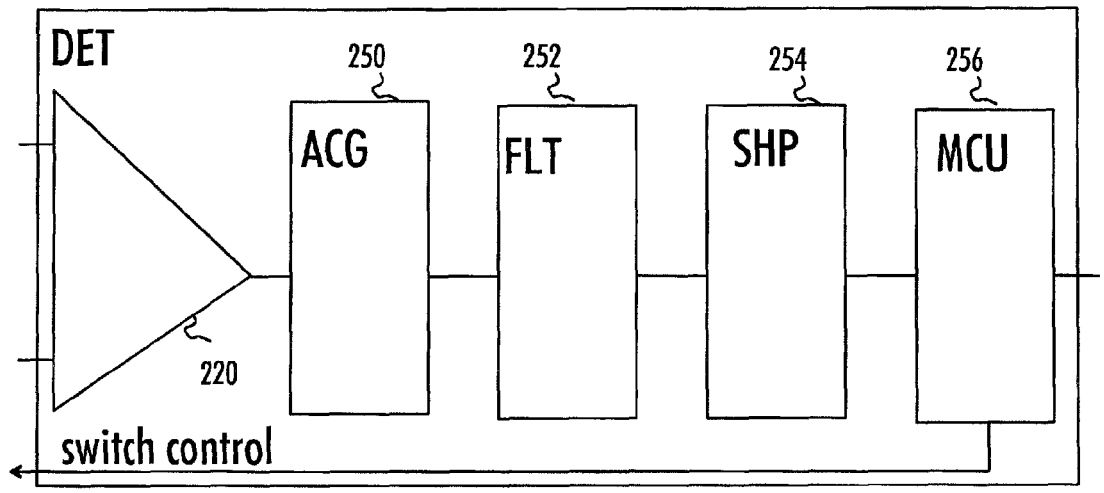
FIGS. 15 and 16 illustrate embodiments of a signal detection circuitry according to an embodiment of the invention.
Figure 16:
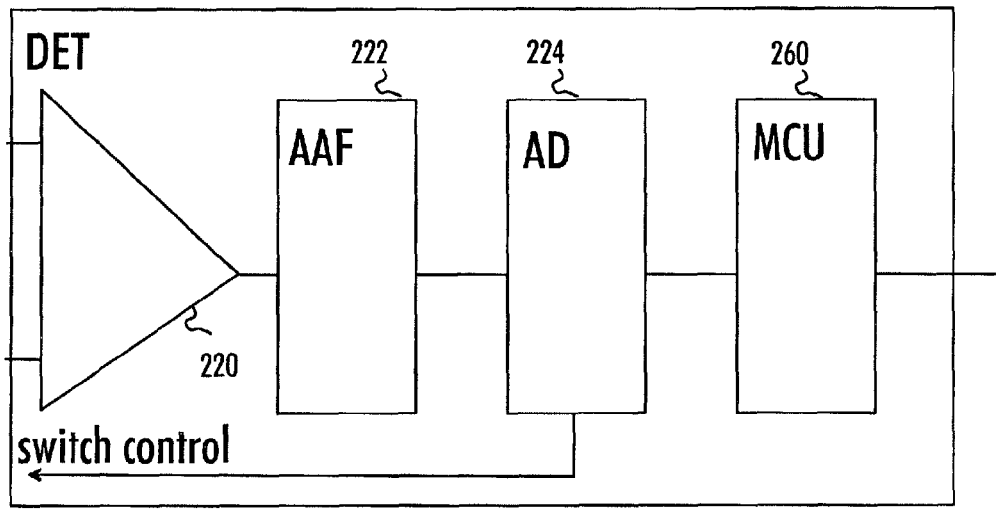
Figure 17:
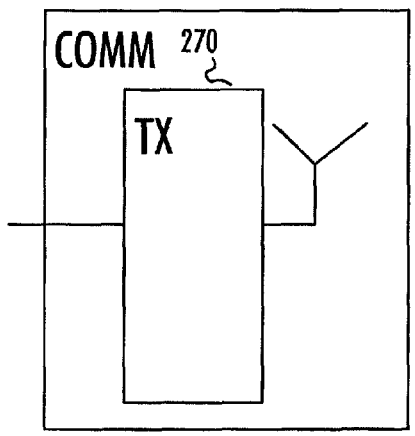
FIG. 17 illustrates an embodiment of a communication circuitry.

FIGS. 15 and 16 illustrate embodiments of the signal detection circuitry 206. FIG. 15 illustrates an embodiment of an analog signal detection circuitry. The analog signal detection circuitry may comprise the differential amplifier 220, another amplifier 250 connected to an output of the differential amplifier 220 and configured to adjust a gain of a signal received from the differential amplifier 220. The amplifier 250 may be an automatically controlled gain (ACG) amplifier. The amplifier 250 may apply its output signal to a filter 252 arranged to filter undesired signal components and apply the filtered signal to a waveform shaper circuitry 254 configured to shape a waveform of the filtered signal in order to modify the signal to have a waveform that is suitable for the detection. The shaped signal may then be applied to a microcontroller unit 256 that may comprise a detector detecting a determined signal component in the shaped signal, e.g. a peak. In this embodiment, the microcontroller unit 256 may be configured to control the interference suppression circuitry to carry out the potential equalization. Accordingly, the microcontroller unit 256 may be configured to output the control signal that operates the switches 218, 402, 404. Outputting a control signal that operates the switches to carry out the equalization may be triggered by a determined event. For example, the microcontroller unit 256 may be configured to output the control signal upon detecting the determined signal component in the shaped signal. In other embodiments, the microcontroller unit 256 may further comprise a signal quality estimator that is configured to evaluate the received signal in order to determine the degree of interference in the received signal. The signal quality estimator may calculate a signal-to-noise ratio (SNR) estimate of the received signal, for example, or another signal quality estimate. When the signal quality estimate indicates that the interference in the received signal exceeds a predetermined threshold, e.g. when the SNR drops below the threshold, the microcontroller unit 256 may be configured to carry out the potential equalization by closing the switches 218, 402, 404.

FIG. 16 illustrates an embodiment of a digital signal detection circuitry. The signal detection circuitry may comprise the differential amplifier 220, the anti-aliasing filter 222, and the A/D converter 224. The A/D converted signal may be applied to a digital microcontroller unit 260 for the signal detection. In this embodiment, the control signal for operating the switches may be output from the A/D converter 224 to enable the potential equalization at time instants when the A/D converter 224 is not sampling the signal, as described in embodiments of FIGS. 12 to 14. However, the control signal may be provided by the microcontroller unit 260 in a manner similar to the embodiments described above in connection with FIGS. 12 to 14, and in connection with the functionality of the microcontroller unit 256 of FIG. 15. The microcontroller unit 260 may be configured to carry out the control of the interference suppression circuitry 204, 400 in a computer process. In response to reading a computer program product embodied on a computer-readable memory apparatus, the microcontroller unit 260 executes the computer process carrying out the equalization of the potential difference between the skin electrodes according to any one of the above-described embodiments.

The signal detection circuitry 206 may be connected to the communication circuitry 208, as described above in connection with FIG. 2. FIG. 12 illustrates an embodiment of the communication circuitry 108, wherein the communication circuitry 208 comprises a transmitter circuitry 270 and an antenna 272. The transmitter circuitry 270 may be provided with appropriate electronics to implement a transmitter according to a wireless communication specification used for conveying the measured biometric signal over an air interface. The transmitter circuitry 270 may also comprise receiver electronics, when the apparatus carrying out embodiments of the invention is configured to receive commands, data, or other signals from another communication apparatus. In an embodiment, the transmitter circuitry 270 is a Bluetooth-based transceiver, such as Bluetooth Low Energy (BLE). In an embodiment, the transmitter circuitry 270 is an ANT transceiver originally introduced by Dynastream Innovations. In an embodiment, the transmitter circuitry 270 is a Zigbee transceiver based on IEEE 802.15.4 standard or its derivative. In an embodiment, the transmitter circuitry 270 is a WiFi transceiver based on IEEE 802.11x standard. In an embodiment of the invention, the transmitter circuitry 270 comprises at least two transceivers selected from the group comprising: Bluetooth or its derivatives, ANT or its derivatives, Zigbee or its derivatives, WiFi or its derivatives. In an embodiment, the transmitter circuitry 270 comprises a transmitter based on inductive transmission.

As used in this application, the term 'circuitry' refers to all of the following: (a) hardware-only circuit implementations, such as implementations in only analog and/or digital circuitry, and (b) to combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) to circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular element, a baseband integrated circuit or applications processor integrated circuit for a mobile phone or a similar integrated circuit in server, a cellular network device, or other network device.

FIGS. 18 to 20 illustrate embodiments of apparatuses comprising the interference suppression circuitry 204, 400 according to some embodiments of the invention.

FIG. 18 illustrates an embodiment where the interference suppression circuitry 204, 400 is detachable from the skin electrodes 200, 202 and from the signal detection circuitry 206. The skin electrodes 200, 202 may comprise connectors 1312, 1314 to which a casing or a body 1300 comprising the interference suppression circuitry 204, 400 may be attached. On the other hand, a casing 1302 of the signal detection circuitry 206 may then be connected to connectors 1306, 1310 of the casing 1300 of the interference suppression circuitry, as illustrated in FIG. 18 in order to achieve the circuit diagram of any one of FIGS. 2, 4, 8, and 9A to 9C, for example. The casing 1300 and the interference suppression circuit 204, 400 together form a modular structure which may further comprise the controller 228 for generating the control signal for the interference suppression circuitry 204, 400, 410, 420. The modular structure of the interference suppression circuitry may thus be attached to and detached from the electrodes 200, 202 and the signal detection circuitry with fast coupling.

FIG. 19 illustrates an embodiment where the measurement apparatus is a strap 1400 to be placed around the chest of the subject. The skin electrodes 200, 202 and the interference suppression circuitry 204, 400 may be integrated in the strap 1400. FIG. 20 illustrates a measurement apparatus configured to measure the biometric signals from hands of the subject and, thus, the skin electrodes 200, 202 may be arranged in a location of a bar 1500 comprising grip portions 1502, 1504 from which the subject grips the measurement apparatus. The interference suppression circuitry 204, 400 may again be integrated to the measurement apparatus to selectively couple the skin electrodes to the common potential.

It will be obvious to a person skilled in the art that, as technology advances, the inventive concept can be implemented in various ways. The invention and its embodiments are not limited to the examples described above but may vary within the scope of the claims.

What is claimed is:

1. An apparatus comprising:
a first signal line configured to couple biometric signals from a first skin electrode to a first input of a differential amplifier comprised as a front-stage in a signal detection circuitry for measurement of the biometric signals;
a second signal line configured to couple reference signals of the biometric signals to a second input of the differential amplifier of the signal detection circuitry; and
an impedance circuitry coupled between the first signal line and the second signal line, wherein impedance of the impedance circuitry is higher on a first frequency band covering a frequency band of the measured biometric signals than on a second frequency band outside the frequency band of the measured biometric signals, wherein the impedance circuitry connects the skin electrodes to each other before the input of the differential amplifier.

2. The apparatus of claim 1, wherein the second signal line is connected to a second skin electrode, different from the first skin electrode.

3. The apparatus of claim 1, wherein a first input terminal of the impedance circuitry is connected to the first signal line, and wherein a second input terminal of the impedance circuitry is connected to the second signal line.

4. The apparatus of claim 1, wherein the impedance circuitry comprises a first sub-circuitry and a second sub-circuitry, wherein a first terminal of the first sub-circuitry is connected to the first signal line, a second terminal of the first sub-circuitry is connected to a first terminal of the second sub-circuitry, and a second terminal of the second sub-circuitry is connected to the second signal line, and wherein the second terminal of the first sub-circuitry and the first terminal of the second sub-circuitry is connected to a bias voltage supply circuitry.

5. The apparatus of claim 1, wherein the impedance circuitry is realized by components forming a circuit equivalent to an inductor, thereby short-circuiting the first signal line to the second signal line for direct current.

6. The apparatus of claim 5, wherein the impedance circuitry is realized by at least one gyrator.

7. The apparatus of claim 1, further comprising the differential amplifier configured to provide a low-pass frequency response, wherein a pass band of the differential amplifier covers the frequency band of the measured biometric signals.

8. The apparatus of claim 1, wherein the impedance of the impedance circuitry is on the first frequency band any one of the following: 0 to 100 ohms, 100 to 300 ohms, 300 to 1000 ohms, 1 to 3 kilo-ohms, 3 to 10 kilo-ohms, 10 to 30 kilo-ohms, 30 to 100 kilo-ohms, and wherein the impedance of the impedance circuit is on the second frequency band any one of the following: 100 to 300 kilo-ohms, 300 to 1000 kilo-ohms, 1 to 3 Mega ohms, and 3 to 10 Mega ohms.

9. The apparatus of claim 1, further comprising a coupling circuitry configured to selectively couple the first signal line and the second signal line to a common electrical potential so as to reduce electrical potential difference between the first signal line and the second signal line.

10. The apparatus of claim 1, further comprising a strap comprising the first skin electrode and the second skin electrode.

11. The apparatus of claim 1, further comprising grip portions designed to be gripped from by a measurement subject, the grip portions comprising the first skin electrode and the second skin electrode.

12. A heart rate measurement unit comprising:
at least one skin electrode;
a signal detection circuitry comprising a differential amplifier having its inputs operationally connected to the at least one skin electrode and to a reference voltage source, and a signal detector operationally connected to an output of the differential amplifier and configured to detect a waveform from a signal received from the output of the differential amplifier, wherein the heart rate measurement unit further comprises an impedance circuitry connected to an input of the signal detection circuitry and coupled between the at least one skin electrode and the reference voltage source, wherein impedance of the impedance circuitry is higher on a first frequency band covering a frequency band of measured biometric signals than on a second frequency band outside the frequency band of the measured biometric signals, wherein the impedance circuitry connects the skin electrodes to each other before the input of the differential amplifier.

13. The heart rate measurement unit of claim 12, further comprising a communication circuitry configured to transmit the measured biometric signals wirelessly to an external receiver apparatus.

14. An apparatus comprising:
a casing;
a plurality of connectors connecting the apparatus between a plurality of skin electrodes and a casing of a signal detection circuitry with a detachable connection;
a first signal line configured to couple biometric signals from a first skin electrode to a first input of the signal detection circuitry comprising a differential amplifier as a front-stage in the signal detection circuitry for measurement of the biometric signals;

a second signal line configured to couple reference signals of the biometric signals to a second input of the differential amplifier of the signal detection circuitry; and an impedance circuitry coupled between the first signal line and the second signal line, wherein impedance of the impedance circuitry is higher on a first frequency band covering a frequency band of the measured biometric signals than on a second frequency band outside the frequency band of the measured biometric signals, wherein the impedance circuitry connects the skin electrodes to each other before the input of the differential amplifier.

* * * * *